United States Patent

Novack et al.

[11] Patent Number: 5,553,366
[45] Date of Patent: Sep. 10, 1996

[54] VIBRATION COMPACTED FABRICS FOR ORTHOPEDIC CASTING TAPES

[75] Inventors: James C. Novack, St. Paul; Scott A. Neamy, Hugo; Matthew T. Scholz, Woodbury, all of Minn.

[73] Assignee: Minnesota Mining and Manufacturing Company, St. Paul, Minn.

[21] Appl. No.: 411,013

[22] Filed: Mar. 27, 1995

Related U.S. Application Data

[62] Division of Ser. No. 142,177, Oct. 25, 1993, abandoned.

[51] Int. Cl.$^6$ ............................... D06H 7/22; A61F 5/04
[52] U.S. Cl. ................... 28/170; 28/155; 28/165; 427/2.31; 427/314; 427/389.8; 427/227
[58] Field of Search ............................ 28/155, 165, 170; 427/2.31, 314, 389.8, 227

[56] References Cited

U.S. PATENT DOCUMENTS

| | | | |
|---|---|---|---|
| 2,765,513 | 10/1956 | Walton | 26/18.6 |
| 3,077,655 | 2/1963 | Runton | 26/18.5 |
| 3,421,501 | 1/1969 | Beightol | 128/90 |
| 3,630,194 | 12/1971 | Boardman | 128/90 |
| 3,686,725 | 8/1972 | Nisbet et al. | 28/74 R |
| 3,787,272 | 1/1974 | Nisbet et al. | 161/89 |
| 3,793,686 | 2/1974 | Nisbet et al. | 28/75 R |
| 3,837,338 | 9/1974 | Chesky et al. | 128/156 |
| 3,908,644 | 9/1975 | Neinart et al. | 128/90 |
| 3,932,526 | 1/1976 | Koshar | 260/607 A |
| 3,972,323 | 8/1976 | Boricheski | 128/91 R |
| 4,041,581 | 8/1977 | Diggle, Jr. | 26/18.6 |
| 4,131,114 | 12/1978 | Kirkpatrick et al. | 128/90 |
| 4,134,397 | 1/1979 | Gianakakos et al. | 128/90 |
| 4,376,438 | 3/1983 | Straube et al. | 128/90 |
| 4,411,262 | 10/1983 | von Bonin et al. | 128/90 |
| 4,433,680 | 2/1984 | Yoon | 128/90 |
| 4,473,671 | 9/1984 | Green | 523/105 |
| 4,502,479 | 3/1985 | Garwood et al. | 128/90 |
| 4,609,578 | 9/1986 | Reed | 428/76 |
| 4,663,106 | 5/1987 | Pomplun et al. | 264/230 |
| 4,667,661 | 5/1987 | Scholz et al. | 128/90 |
| 4,668,563 | 5/1987 | Buese et al. | 428/230 |
| 4,704,113 | 11/1987 | Schoots | 604/379 |
| 4,705,840 | 11/1987 | Buckanin | 528/53 |
| 4,745,912 | 5/1988 | McMurray | 128/90 |
| 4,800,872 | 1/1989 | Buese et al. | 128/90 |
| 4,841,958 | 6/1989 | Ersfeld et al. | 128/90 |
| 4,940,047 | 7/1990 | Richter et al. | 128/90 |
| 4,947,839 | 8/1990 | Clark et al. | 128/90 |
| 4,984,566 | 1/1991 | Sekine et al. | 128/90 |
| 5,014,403 | 5/1991 | Buese | 28/170 |
| 5,027,804 | 7/1991 | Forsyth et al. | 128/90 |
| 5,060,349 | 10/1991 | Walton et al. | 26/18.6 |
| 5,088,484 | 2/1992 | Freeman et al. | 128/89 R |
| 5,169,698 | 12/1992 | Behjati et al. | 428/68 |
| 5,256,134 | 10/1993 | Ingham | 602/8 |
| 5,354,259 | 10/1994 | Scholz et al. | 602/8 |
| 5,370,927 | 12/1994 | Scholz et al. | 428/254 |
| 5,382,445 | 1/1995 | Yasis | 427/2.31 |
| 5,405,643 | 4/1995 | Scholz | 427/2.31 |

FOREIGN PATENT DOCUMENTS

0407056A2  1/1991  European Pat. Off. .

*Primary Examiner*—Patrick Ryan
*Assistant Examiner*—Rich Weisberger
*Attorney, Agent, or Firm*—Gary L. Griswold; Walter N. Kirn; F. Andrew Ubel

[57] ABSTRACT

The present invention provides an article, comprising: a fabric sheet which has been compacted using a heat shrink yarn; and a curable or hardenable resin coated onto the fabric sheet. The present invention involves compacting a fabric sheet to impart stretchability and conformability to the fabric while minimizing undesirable recovery forces. Suitable fabrics for compacting are fabrics which comprise fiberglass fibers which are capable of first being compacted and then being set or annealed in the distorted, state. The article may be in the form of an orthopedic bandage and may optionally contain a microfiber filler associated with the resin.

10 Claims, 4 Drawing Sheets

VIBRATION COMPACTED FABRICS FOR ORTHOPEDIC CASTING TAPES

This is a division of application No. 08/142,177 filed 10/25/1993, now abandoned.

FIELD OF THE INVENTION

This invention relates to sheet materials coated with a curable or hardenable polymeric resin. More particularly, this invention relates to a curable or hardenable resin coated sheet material useful in preparing an orthopedic bandage.

BACKGROUND OF THE INVENTION

Many different orthopedic casting materials have been developed for use in the immobilization of broken or otherwise injured body limbs. Some of the first casting materials developed for this purpose involve the use of plaster of Paris bandages consisting of a mesh fabric (e.g., cotton gauze) with plaster incorporated into the openings and onto the surface of the mesh fabric.

Plaster of Paris casts, however, have a number of attendant disadvantages, including a low strength-to-weight ratio, resulting in a finished cast which is very heavy and bulky. Furthermore, plaster of Paris casts typically disintegrate in water, thus making it necessary to avoid bathing, showering, or other activities involving contact with water. In addition, plaster of Paris casts are not air permeable, thus do not allow for the circulation of air beneath the cast which greatly facilitates the evaporation and removal of moisture trapped between cast and skin. This often leads to skin maceration, irritation, or infection. Such disadvantages, as well as others, stimulated research in the orthopedic casting an for casting materials having improved properties over plaster of Paris.

A significant advancement in the an was achieved when polyisocyanate prepolymers were found to be useful in formulating a resin for orthopedic casting materials, as disclosed, for example, in U.S. Pat. No. 4,502,479 (Garwood et al.) and U.S. Pat. No. 4,441,262 (Von Bonin et al.). U.S. Pat. No. 4,502,479 sets forth an orthopedic casting material comprising a knit fabric which is made from a high modulus fiber (e.g., fiberglass) impregnated with a polyisocyanate prepolymer resin which will form a polyurea. Orthopedic casting materials made in accordance with U.S. Pat. No. 4,502,479 provide significant advancement over the plaster of Paris orthopedic casts, including a higher strength-to-weight ratio and greater air permeability. However, such orthopedic casting materials tend not to permit tactile manipulation or palpation of the fine bone structure beneath the cast to the extent possible when applying a plaster of Paris cast. In this regard, knit fiberglass materials are not as compressible as plaster, and tend to mask the fine structure of the bone as the east is applied, e.g., the care provider may be limited in "feeling" the bone during reduction of the fracture.

Fiberglass backings have further disadvantages. For example, fiberglass backings are comprised of fibers which have essentially no elongation. Because the fiber elongation is essentially nil, glass fabrics do not stretch unless they are constructed with very loose loops which can deform upon application of tension, thereby providing stretching of the fabric. Knitting with loosely formed chain stitches imparts extensibility by virtue of its system of interlocking knots and loose loops.

To a greater extent than most knitted fabrics, fiberglass knits tend to curl or fray at a cut edge as the yarns are severed and adjacent loops unravel. Fraying and raveling produce unsightly ends and, in the case of an orthopedic cast, frayed ends may interfere with the formation of a smooth cast, and loose, frayed ends may be sharp and irritating after the resin thereon has cured. Accordingly, frayed edges are considered a distinct disadvantage in orthopedic casting tapes. Stretchy fiberglass fabrics which resist fraying are disclosed in U.S. Pat. No. 4,609,578 (Reed), the disclosure of which is incorporated by reference for its teaching of heat-setting. Thus, it is well known that fraying of fiberglass knits at cut edges can be reduced by passing the fabric through a heat cycle which sets the yarns giving them new three-dimensional configurations based on their positions in the knit. When a fiberglass fabric which has been heat-set is cut, there is minimal fraying and when a segment of yarn is removed from the heat-set fabric and allowed to relax, it curls into the crimped shape in which it was held in the knit. Accordingly, at the site of a cut, the severed yarns have a tendency to remain in their looped or knotted configuration rather than to spring loose and cause fraying.

In processing extensible fiberglass fabrics according to U.S. Pat. No. 4,609,578 (Reed), a length of fabric is heat-set with essentially no tension. The fabric is often wound onto a cylindrical core so large batches can be processed at one time in a single oven. Care must be taken to avoid applying undue tension to the fabric during wind-up on the knitter which would distort the knots and loops. To prevent applying tension to the fabric during winding, the winding operation is preferably performed with a sag in the fabric as it is wound on the core.

U.S. Pat. No. 4,668,563 (Buese) describes a conformable fiberglass casting tape comprising a combination of high modulus fibers and an elastomeric extensible fiber. Unfortunately, permanently elastic fabrics can exhibit significant rebound force when stretched and therefore have the potential to cause undesirable constriction forces when wrapped around a limb. This is especially undesirable considering that the constriction forces are then "locked" into place upon curing and cannot be easily relieved by the wearer.

Alternatively, U.S. Pat. No. 5,014,403 (Buese) describes a method of making a stretchable orthopedic fiberglass casting tape by knitting an elastic yarn under tension into the fiberglass fabric in the length direction, releasing the tension from the elastic yarn to compact the fabric and removing the elastic yarn from the fabric. Unfortunately, fabrics having a sufficient basis weight to be useful in orthopedic casting applications are irregularly compacted by this method and contain regions of varying extensibility. This irregularity not only provides a bad aesthetic appearance but also produces a rough surface in the finished cast.

From the foregoing, it will be appreciated that what is needed in the art is an orthopedic casting material which has both the advantages of plaster of Paris, e.g.,good moldability and palpability of the fine bone structure, and the advantages of non-plaster of Paris materials, e.g., good strength-to-weight ratio and good air permeability. In this regard it would be a significant advancement in the art to provide such a combination of advantages without actually using plaster of Paris, thereby avoiding the inherent disadvantages of plaster of Paris outlined herein. It would be a further advancement in the art to provide such non-plaster of Paris orthopedic casting materials which have as good or better properties than the non-plaster of Paris orthopedic casting materials of the prior art. Such orthopedic casting materials and methods for preparing the same are disclosed and claimed herein.

RELATED APPLICATIONS

Of related interest are the following U.S. patent applications, filed on Jan. 25, 1993 by the assignee of this invention: "Mechanically Compacted Fabrics for Orthopedic Casting Tapes"—Ser. No. 08/008,161; and "Microcreping of Fabrics for Orthopedic Casting Tapes"—Ser. No. 08/008,751; and copending U.S. patent application filed on even date herewith by the assignee of this invention entitled "Wet Compacting of Fabrics for Orthopedic Casting Tapes"—Ser. No. 08/142573 and "Compacted Fabrics for Orthopedic Casting Tapes"—Ser. No. 08/141830 which are herein incorporated by reference.

SUMMARY OF THE INVENTION

The present invention provides an article comprising a compacted fiberglass fabric sheet and a curable or hardenable resin coated onto the fabric sheet. The fabric sheet is compacted using an elastomeric yarn and a vibration process and is heat treated or "set" thereby removing the elastomeric yarn and providing extensibility to the fabric. The article may be in the form of an orthopedic bandage.

The present invention also provides a method of producing a highly extensible high modulus fabric, such as a fiberglass fabric, comprising the steps of: warp knitting a fabric comprised of a high modulus yarn, e.g., fiberglass, and stretched elastomeric yarn; releasing the tension on the elastomeric yarn as the fabric comes off the knitting machine; vibrating the fabric, thereby allowing the fabric to uniformly compact; heat setting the compacted fabric; and coating the fabric with a curable or hardenable resin.

DETAILED DESCRIPTION OF THE INVENTION

The present invention relates to orthopedic casting materials and methods for preparing such orthopedic casting materials, wherein the materials comprise a fiberglass backing or fabric which is impregnated with a curable or hardenable liquid resin. In particular, the fabrics employed in the present invention have important characteristics and physical properties which allow the fabrics to be made highly extensible.

One element of this invention is a flexible sheet upon which a curable or hardenable resin can be coated to reinforce the sheet when the resin is cured or hardened thereon. The sheet is preferably porous such that the sheet is at least partially impregnated with the resin. Examples of suitable sheets are knit fabrics comprised of inorganic fibers or materials such as fiberglass. The sheet may alternatively be referred to as the "scrim" or the "backing".

The present invention involves compacting a fabric sheet using an elastomeric yarn and a vibration process to impart stretchability and conformability to the fabric while minimizing undesirable recovery forces.

Suitable fabrics, after compaction, have important characteristics and physical properties which allow the fabrics to be loaded with resin to the extent needed to provide proper strength as an orthopedic casting material, while providing necessary porosity as well as improved extensibility leading to improved conformability, tactile manipulability, moldability, and palpability. Several important criteria for choosing a fabric which will provide the characteristics necessary for purposes of the present invention include: (1) lengthwise extensibility and conformability after compaction, and the related characteristics of moldability, tactility, and palpability once the fabric has been resin impregnated; (2) resin loading capacity; and (3) porosity. It is important that each of these parameters be carefully controlled in providing fabrics which will successfully form orthopedic casting materials (e.g., casts having high strength and good layer-to-layer lamination strength) within the scope of the present invention.

Extensibility is important from the standpoint that the fabric must be extensible enough along its length, i.e., in the elongated direction, so that the resultant orthopedic casting material can be made to substantially conform to the body part to which it is applied. Materials which are not sufficiently extensible in the elongated direction do not conform well to the body part when wrapped therearound, often resulting in undesirable wrinkles or folds in the material. On the other hand, the extensibility of the fabric in the elongated direction should not be so high that the material is too stretchy, resulting in a material structure which may be deformed to the extent that strength is substantially reduced.

For purposes of the present invention, the coated fabric, after compaction and after being coated with a curable liquid resin, should have from about 10% to about 200% extensibility in the elongated direction when a 2.63 N load or force is applied per 1 cm wide section of the fabric, and preferably from about 25% to about 75% extensibility in the elongated direction when a 2.63 N load or force is applied per 1 cm wide section of the fabric, and more preferably from about 35% to about 65% extensibility in the elongated direction when a 2.63 N load or force is applied per 1 cm wide section of the fabric.

Although not nearly as critical, it is also desirable that the fabric employed have some extensibility along its width, i.e., in the direction transverse to the elongated direction. Thus although the fabric may have from 0% to 100% extensibility in the transverse direction, it is presently preferable to use a fabric having from about 1% to about 30% extensibility in the transverse direction when a 2.63 N load or force is applied per 1 cm wide section of the fabric. The compaction process described herein principally imparts extensibility in the elongated direction. However, it is anticipated that one might compact a fabric in the elongated direction and in the transverse direction, thereby imparting biaxial extensibility.

The fabrics of the present invention, after compaction, although stretchable, are preferably not overly elastic or resilient. Fabrics which are overly elastic, when used as backings for orthopedic bandages, tend to cause undesirable constriction forces around the wrapped limb or body part. Thus, once the resin impregnated fabric has been stretched and applied around a body part, the stretched material preferably maintains its shape and does not resort back to its unstretched position.

The resin loading capacity or ability of the fabric to hold resin is important from the standpoint of providing an orthopedic casting material which has sufficient strength to efficaciously immobilize a body part. The surface structure of the fabric, including the fibers, interstices, and apertures, is very important in providing proper resin loading for purposes of the present invention. In this regard, the interstices between the fibers of each fiber bundle must provide sufficient volume or space to hold an adequate amount of resin within the fiber bundle to provide the strength necessary; while at the same time, the apertures between fiber bundles preferably remain sufficiently unoccluded such that adequate porosity is preserved once the cast is applied. Thus, the interstices between fibers are important in providing the necessary resin loading capacity, while the apertures are important in providing the necessary porosity for the finished cast. However, a balancing of various parameters is needed to achieve both proper resin loading and porosity. The coated fabric should have preferably between about 6 and 70 openings (i.e., apertures) per square cm, more preferably between about 10 and 50 openings per square cm, and most preferably between about 20 and 40 openings per square cm when measured under a tensile load of 2.63 N/cm width. As used herein an "opening" is defined as the area defined by adjacent wales and in-lay members. The number of openings per unit area is therefore determined by multiplying the number of wales by the number of courses and dividing by the area.

As used herein, a "compacted" fiberglass sheet is one in which extensibility is imparted to the fabric due to the structural overlapping of successive loops and/or the structural relaxation of loops by the "vibration compaction" processes described herein. The compaction process is believed to impart extensibility to the fabric by "compacting" the loops of the knit as described herein. Typically, when a fabric is knitted the inside surfaces of two adjacent rows of loops are in contact or nearly in contact and the loops are distorted in the lengthwise direction (e.g., in the shape of an oval). This contact and/or distortion is the result of the fabric being under tension while the knit is being formed. Each successive row of loops (i.e., chain stitches) is, in effect, formed against the preceding row of loops. The compaction process of the present invention imparts fabric compaction by overlapping adjacent rows of loops (i.e., to a "non-contacting" position) and/or relaxing the strained loops to a lower stress (e.g., more circular) configuration and setting or annealing the fabric in the compacted form. Extensibility is imparted to the fabric due to the overlap of the rows and/or the greater ability of the more circular loops to be deformed. When tension is again applied to the fabric the loops can return to their original "contacting" position, i.e., the position they occupied when originally knit.

Fiberglass knitted fabrics with good extensibility are achievable with two common knitting methods: Raschel and tricot. Raschel knitting is o described in "Raschel Lace Production" by B. Wheatley (published by the National Knitted Outerwear Association, 51 Madison Avenue, New York, N.Y. 10010) and "Warp Knitting Production" by Dr. S. Raz (published by Heidelberger Verlagsanstadt und Druckerei GmbH, Hauptstr. 23, D-6900 Heidelberg, Germany). Two, three and four bar Raschel knits can be produced by regulating the amount of yarn in each stitch. Orthopedic casting tape fabrics are generally two bar Raschel knits although extra bars may be employed. Factors which affect the extensibility of fiberglass Raschel knits are the size of the loops in the "chain" stitch, especially in relation to the diameter(s) of the yarn(s) which passes through them, and the amount of a loose yarn in the "lay-in" or "laid-in" stitch(es). If a chain loop is formed and two strands of lay-in yarn pass through it which nearly fill the loop, then the loop resists deformation and little stretch will be observed. Conversely, if the lay-in yarns do not fill the loop, then application of tension will deform the loop to the limits of the lay-in yarn diameter and stretch will be observed.

Typical bar patterns for the knit fabric substrates of the present invention are shown in the drawings.

Figure 1:
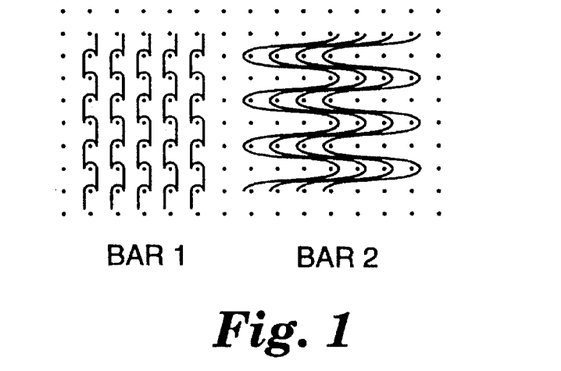
FIG. 1 is a two bar Raschel knit in which bar one performs a simple chain stitch and bar two performs lapping motions to lay in yarn.

FIG. 1 is a two bar Raschel knit in which bar one performs a simple chain stitch and bar two performs lapping motions to lay in yarn.

Figure 2:
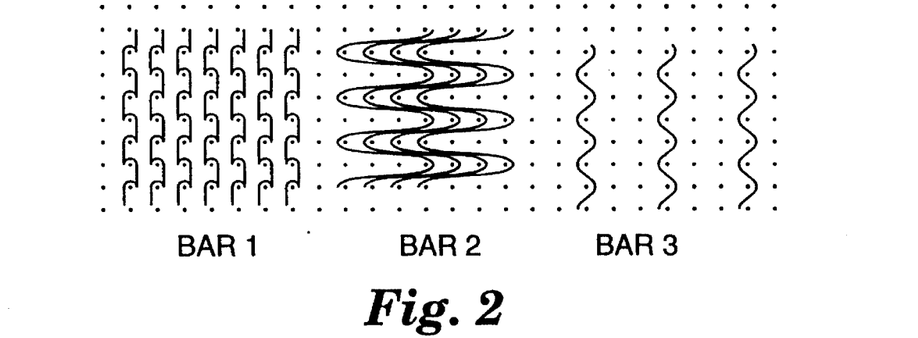
FIG. 2 is a three bar Raschel knit in which bar one performs a simple chain stitch and bars two and three perform lapping motions to lay in yarn, and wherein bar three illustrates the lay in of an elastomeric yarn.

FIG. 2 is a three bar Raschel knit in which bar one performs a simple chain stitch and bars two and three perform lapping motions to lay in yarn, and wherein bar three illustrates the lay in of an elastomeric yarn.

Figure 3:
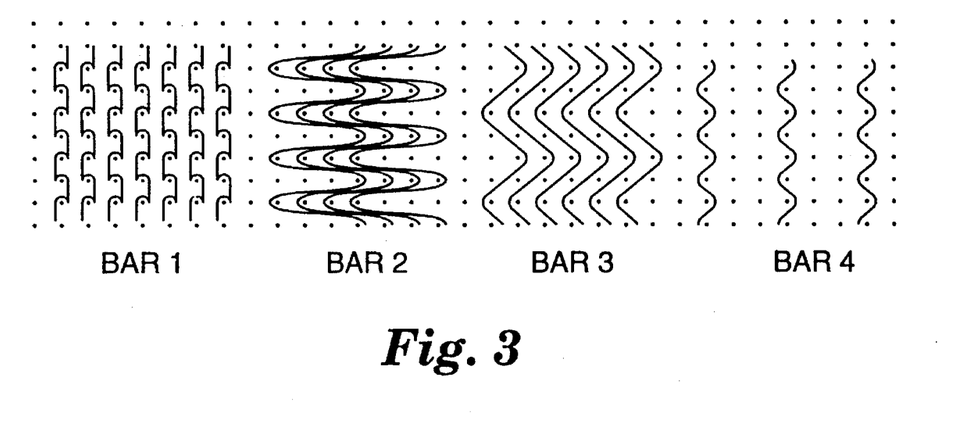
FIG. 3 is a four bar Raschel knit in which bar one performs a simple chain stitch and bars two, three and four perform lapping motions to lay in yarn, and wherein bar four illustrates the lay in of an elastomeric yarn.

FIG. 3 is a four bar Raschel knit in which bar one performs a simple chain stitch and bars two, three and four perform lapping motions to lay in yarn, and wherein bar four illustrates the lay in of an elastomeric yarn.

Figure 4:
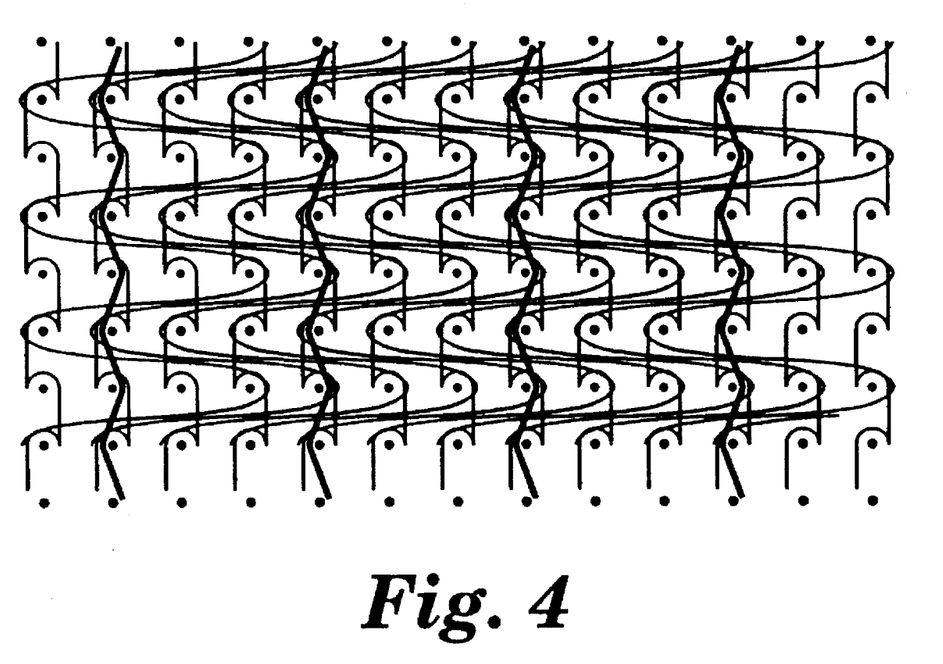
FIG. 4 is a depiction of a three bar Raschel knit in which bar one performs a simple chain stitch, bar two performs lapping motion to lay in yarn, and bar three performs lapping motions to lay in an elastomeric yarn. The bars are depicted in a overlapping view.

FIG. 4 is a depiction of a three bar Raschel knit in which bar one performs a simple chain stitch, bar two performs lapping motion to lay in yarn, and bar three performs lapping motions to lay in an elastomeric yarn. The bars are depicted in a overlapping view.

Figure 5:
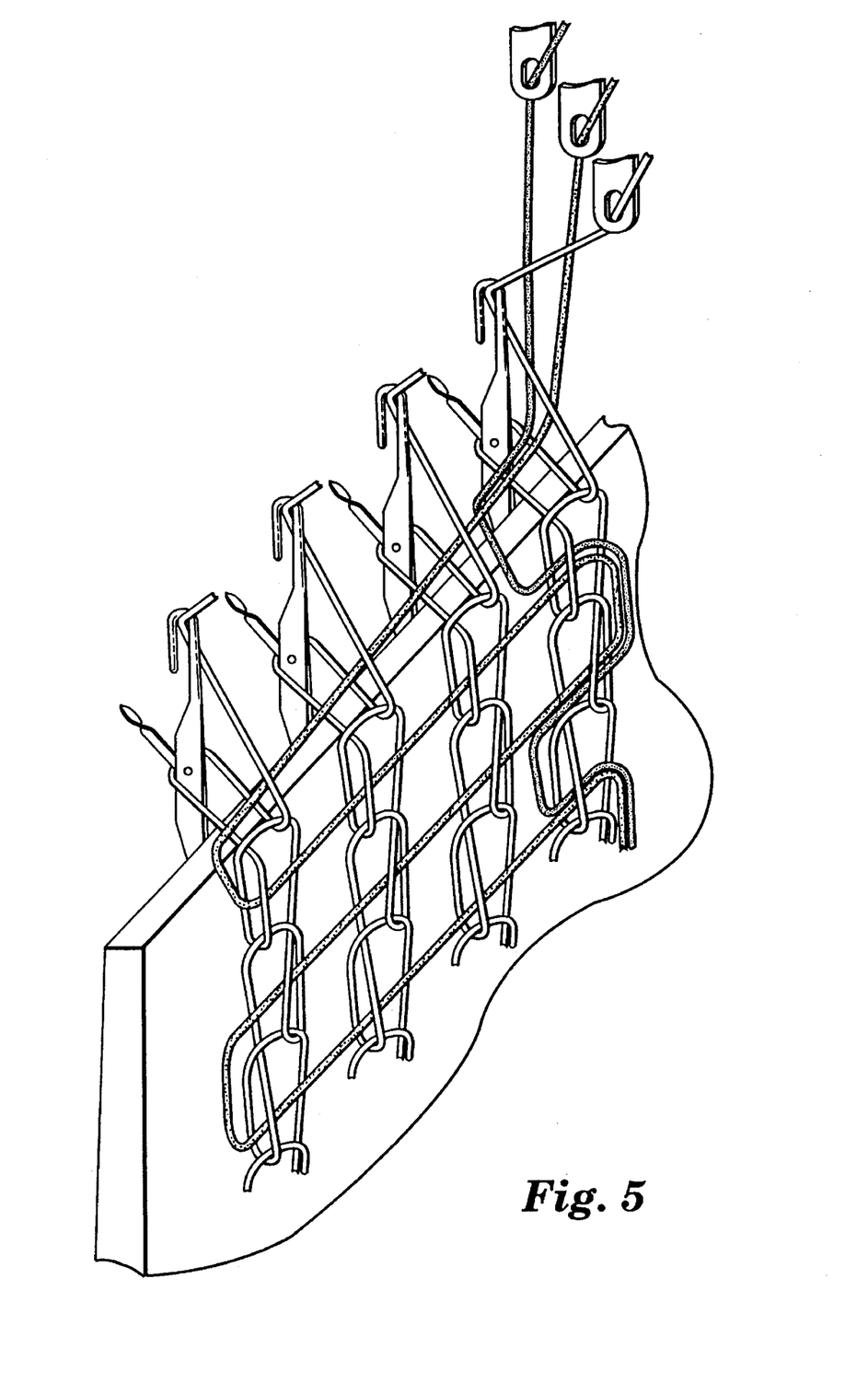
FIG. 5 is a depiction of a three bar "latch hook" Raschel knitter in which four needles are shown knitting four chain stitches and two guidebars providing lay-in yarns. For the purposes of this invention, one might alternatively employ a "compound needle" Raschel knitter which is not shown.

FIG. 5 is a depiction of a three bar "latch hook" Raschel knitter in which four needles are shown knitting four chain stitches and two lay-in stitches. For the purposes of this invention, one might alternatively employ a "compound needle" Raschel knitter which is not shown.

It should be understood that the above bar patterns may be modified. For example, FIG. 2 may be modified by employing fewer or more elastomeric yarns. Alternatively, the elastomeric yarn may be laid in one or more of the wales of the fabric or more than one elastomeric yarn may be laid in a single wale.

The fabrics of the present invention are knit ordinarily using a 3 bar construction although constructions with greater than 3 bars are possible. For example, the "front bar" may contain a high modulus yarn, e.g., a fiberglass yarn, and form the chain stitch. A "back bar" may contain a high modulus yarn and form the lay-in stitch that may transverse 1 to 10 needles but preferably traverses 2 to 6 needles and most preferably 3 to 4 needles. An organic elastomeric yarn is normally inserted as an additional in-lay using a "middle bar". Note also that it is possible to insert the elastomeric yarn using the back bar and make the fiberglass in-lay stitch using the middle bar. This is not preferred, however, due to the rougher texture of the fabric produced. The elastomeric yarn is laid in under tension (i.e., stretched) such that when the fabric comes off the knitting machine an internal compaction force is generated due to contraction of the elastic yarn.

For orthopedic casting material, the fabric selected (preferably fiberglass), in addition to having the extensibility requirement noted above, should be of a suitable thickness and mesh size to insure good penetration of the curing agent (e.g., water) into the roll of resin-coated tape and to provide a finished cast with adequate strength and porosity. Such fabric parameters are well-known to those skilled in the art and are described in U.S. Pat. No. 4,502,479 which is herein incorporated by reference.

The term "high modulus" as used herein to describe the fabric component of the casting material refers to the degree of resistance to deformation or bending and is expressed in terms of the modulus of elasticity. Modulus of elasticity is the ratio of change in stress to the change in strain which occurs when a fiber is mechanically loaded. The initial modulus of elasticity of the fiber should be greater than about $8 \times 10^6$ lbs/square inch (55.2 GPa). Such fibers include continuous filament E-fiberglass, polyaramid filament known as Kevlar® 49 (available from E.I. DuPont de Nemours and Company), ceramic fibers such as Nextel® (available from 3M Company), continuous filament graphite such as Thornel® (available from Union Carbide Corp.), boron fiber (such as made by Avco Corp.), and metal fibers such as stainless steel filaments which when fine enough can be formed into fabrics by weaving or knitting. These high modulus fibers impart a high degree of strength and rigidity to the cast. They may be combined with low to intermediate modulus materials when the flexibility of such yarns enables easier fabrication of the fabric. Low modulus fibers are those having an initial modulus of elasticity of less than about $3 \times 10^6$ lbs/in$^2$ (20.7 GPa) and include cotton, polyester (such as "Dacron"), polypropylene, "Orlon", "Dynel"® (Union Carbide), "Nomex"® (Dupont) and nylon. An example of a fiber with an intermediate modulus is polyvinyl alcohol fiber known as "Kuralon" (available from Kuraray Co., Ltd.). Although hybrid fabrics are useful in making orthopedic casts, a majority of high modulus fiber is necessary for adequate cast rigidity and strength.

In addition to structural strength provided by the high modulus fiber, the fabric must have certain textural characteristics. The textural characteristics of the fabric, especially its surface area, porosity and thickness, affect the thoroughness and rapidity with which the curing agent becomes mixed or dissolved in the resinous component impregnated into the fabric. In one extreme in which the curing agent, e.g., water, contacts only the surface of the resin, the surface of the resin would become hardened, but the resin would remain fluid below the hardened surface and not contribute to the strength of the cast. Furthermore, the hardened surface often impedes the permeation of the curing agent into the bulk of the still fluid resin. In such a case the desired rapid hardening is not achieved, and the bulk of the resin may never become hard because the surface is impenetrable to the curing agent. It has been discovered that such behavior can be avoided if the resinous layer is kept thin. This can be achieved at useful loadings of resin into the fabric if the fabric is selected to be thin and to have a high surface-to-volume ratio.

In determining the optimum thickness of the fabric, the need to keep the resinous layer thin to promote complete curing must be balanced with the need to minimize the number of layers in the cast. Practical considerations related to the ease of wrapping an orthopedic cast limit the number of layers of tape that it is convenient to apply. For most efficient cast application it is desired that the cast be comprised of no more than 6 to 8 layers of overlapping wraps of tape and preferably 4 to 5 layers of tape. A sufficient amount of material must be applied in these few layers to achieve the desired ultimate cast strength and rigidity. The thinner the fabric, the more wraps of tape have to be made to achieve adequate strength and rigidity. It has been found that a fabric thickness between 0.020 and 0.045 inch (.051 and 0.114 cm) and preferably between 0.022 and 0.035 inch (0.056 and 0.089 cm), achieves the optimum balance between good resin curing and a minimum number of wraps.

The fabric should be a mesh, i.e., it should have openings through it to enable the curing agent to penetrate into the roll and expose all parts of the resin. Openings in the fabric also facilitate circulation of air through the finished cast and evaporation of moisture from beneath the cast. This contributes to the patient's comfort and the maintenance of healthy skin under the cast. In the case of casting materials whose strength or rigidity is not degraded by exposure to water, cast porosity also enables rapid drying after bathing or following various forms of hydrotherapy or fluid rinsing for tissue debridement. The fabric should have a mesh size 20 to 200 openings per square inch (3.1 and 31 openings per cm$^2$), and preferably 80 to 150 openings per square inch (12.4 and 23.25 openings per cm$^2$).

Suitable fabrics have a sufficient basis weight to be useful in orthopedic casting applications. Preferred fabrics have a basis weight of at least about 0.05 gm/in$^2$ (0.008 gm/cm$^2$), more preferably, of at least 0.11 gm/in$^2$ (0.018 gm/cm$^2$), when a 1 inch by 1 inch (2.54 cm by 2.54 cm) piece of the fabric is measured in a relaxed condition.

The present invention is to a method of compacting high modulus knits by the "vibration compaction" processes described herein to achieve a highly extensible high strength fabric. It is presently believed that this process will work for a variety of high modulus materials including fiberglass, ceramic fibers such as Nextel™, and polyaramides fibers such as Kevlar™. While not being bound to any theory, the process is believed to result in fabric compaction due to, in part, the high modulus yarns moving to a lower stress configuration as a result of the vibration of the fabric and the release of the tension of the stretched elastomeric yarns. For example, after being knit, fiberglass fabrics typically have oval shaped loops in the wale stitch resulting from the tension applied by the take up rollers when removing the fabric from the needle bed. A loop having a circular shape, i.e., a larger minimum radius of curvature, would have a lower energy than a more stressed oval loop. Achieving this lower stress configuration and/or causing the rows of loops to overlap results in compaction of the fabric.

The "vibration compaction" process comprises the steps of: knitting a high modulus yarn and a stretched elastomeric yarn to form a fabric comprising adjacent rows of loops; releasing the tension on the elastomeric yarn; vibrating the fabric to uniformly compact the fabric; and heat setting the fabric thereby removing the elastomeric yarn.

When the casting material is a fiberglass fabric, suitable elastomeric yarns are made of fibers which combust at temperatures lower than the degradation temperature of the inorganic fibers (e.g., glass fibers) of the fabric. Preferably the combustion temperatures of the elastomeric yarn are less than or equal to the temperature commonly used for heat setting fiberglass yarns. More preferably the combustion temperature of the elastomeric yarn is between about 200°

C. and 540° C. Most preferably the combustion temperature of the elastomeric yarn is between about 300° C. and 500° C. Heating the fabric to temperatures above about 540° C. should be avoided as subjecting the fiberglass to temperatures of greater than about 540° C. can weaken the fiberglass yarns in the fabric which may result in reduced strength of casts made from such fabrics.

Suitable elastomeric yarns for use in the present invention include yarns which when present in a sufficient quantity are capable of compacting the fabric. Preferred elastomeric yarns are between 70 and 800 denier but are more preferably between 200 and 600 denier and most preferably between 350 and 550 denier. The elastomeric yarn may be any yarn which when incorporated into the knit generates a sufficient contraction force to compact the fabric.

Suitable elastomeric yarns include synthetic elastomers or natural elastomers. Suitable synthetic elastomers include yarns made from: polybutadiene; polychloroprene; polyisoprene; polyurethane (e.g., aliphatic or aromatic polyurethanes including commercial materials such as Spandex™ and Lycra™); copolymers of chloroprene and other monomers; copolymers of a diene and styrene; copolymers of a diene and acrylonitrile; copolymers of styrene and acrylonitrile; copolymers and block copolymers of styrene and butadiene; copolymers and block copolymers of styrene and isoprene; terpolymers of styrene, butadiene and isoprene (e.g., Kraton™); and ethylene propylene elastomers such as copolymers of ethylene and propylene and terpolymers of ethylene, propylene and a diene. Suitable natural elastomers include yarns made from natural rubber. Preferred yarns are inexpensive and have a high force to weight ratio and low heats of combustion. Preferred yarns include polyurethane yarns and natural rubber yarns. The most preferred yarns are polyurethane yarns.

The elastomeric yarn(s) may be knit into the fabric either as a lay-in stitch or as a chain stitch. Preferably, the elastomeric yarn is knit into the fabric as a lay-in stitch. The essential requirements of an elastomeric yarn are that it be capable of knitting with the fabric yarn and that it compact the fabric. Therefore, when the tension on the elastomeric yarn is released and the fabric vibrated and then the elastomeric yarn combusted, e.g., through application of heat, the fabric remains present in the form of a compacted, heat set fabric. The elastomeric yarn is preferably knit into the fabric such that the knit is compacted at least 10%, more preferably at least 14%, and most preferably at least 18%.

When the elastomeric yarn is present as laid-in yarns it is preferably knitted through a single wale. This embodiment is illustrated, for example, in FIG. 2. In that figure, a third bar is depicted knitting an elastomeric yarn across a single chain stitch (bar 1). Additional lay-in yarns are knitted into the fabric using bar 2. In this manner maximum lengthwise compaction may be achieved as the elastomeric yarn is relaxed. The elastic yarn may be in-laid "in-phase" or "out-of-phase" with respect to the fiberglass in-lay. Preferably the elastomeric yarn is in-laid in-phase with respect to the fiberglass in-lay. This orientation has been found to produce fabrics with fewer compaction defects. Alternatively, the elastomeric yarn may cross more than one chain stitch. It is believed that this embodiment will produce a fabric with biaxial compaction.

As previously mentioned, the elastomeric yarn should be positioned in the knit so as to minimize the amount required and maximize the force generated during contraction. If the yarn is placed in as a wale in addition to the fiberglass wales (i.e., as an additional wale since after desizing some wales would need to be present) a significant amount of organic material is added which could result in a brittle tape after heat treatment. If the yarn is placed as a lay-in and maximum lengthwise compaction is desired then the yarn is preferably laid in across a single needle in order to ensure that most of the shrinkage force of the laid-in yarn is used to compact the tape in the length direction.

The elastomeric yarn may be knitted through each wale (not shown in FIG. 2) or through fewer than all the wales (as shown in FIG. 2). Notably, there need not be an elastomeric yarn for every wale. The elastomeric yarn need only be present in the fabric in an amount sufficient to give the desired compaction to the fabric when the yarn is relaxed and the fabric vibrated. It has been found that knitting the elastomeric yarn through every third or fourth wale is preferred. Having too many elastomeric yarns increases the potential for undesirable localized heating of the fiberglass during the combustion step. Having too few elastomeric yarns results in uneven compaction or inadequate compaction. The exact number of elastomeric yarns needed will depend upon the fabric weight and knit pattern employed, the weight and tensile properties of the elastomeric yarn employed, and the desired amount of compaction. In general, for typical fiberglass fabrics the elastomeric yarns are preferably laid in every second to every sixth wale and most preferably every third or fourth wale.

The elastomeric yarn may also be in the form of a chain stitch yarn. When the elastomeric yarn is knitted in the form of a chain stitch it is preferable to lay in noncombustible yarns (e.g., fiberglass yarns) across the elastomeric chain stitch yarn and thereby connect adjacent noncombustible chain stitches. Thus, when the elastomeric chain stitch is later removed when heat setting the fiberglass, the fabric will maintain its integrity.

Figure 6A:
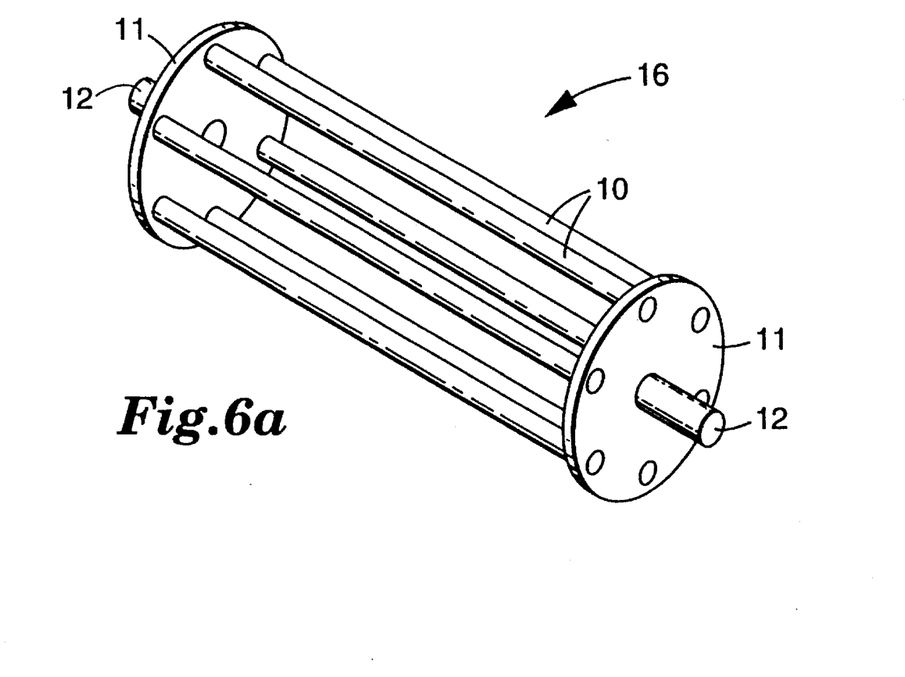
FIG. 6 is a depiction of a "beater bar" apparatus comprising a plurality of vibrational elements. For the purposes of this invention, one might alternatively employ any suitable means to transmit a vibratory motion to the knit fabric.
Figure 6B:
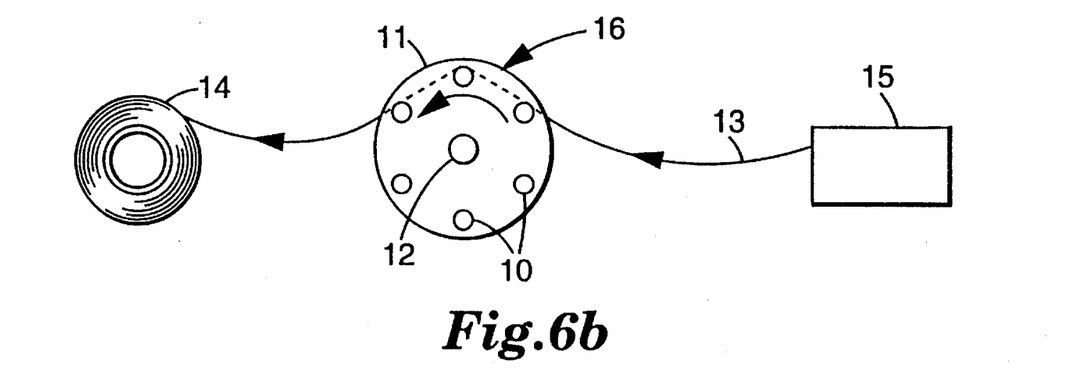

When the fabric comes off the knitting machine the tension on the elastomer yarns is released and the yarns begin to contract. The contraction, however, is somewhat impeded by the high modulus of elasticity of the fiberglass yarns and the friction between yarns. In order to facilitate uniform and maximum fiber movement the fabric is vibrated. Any suitable vibration method may be employed so long as the vibration does not overly damage the relatively fragile fiberglass yarns. For example, it is preferred that rough surfaces or surfaces with edges that can "snag" the fabric be avoided. It is preferred that objects that contact the fabric to impart vibration have generally smooth surfaces and/or dull or rounded edges. A presently preferred method of vibration consists of passing the fabric over a rotating "beater bar". A preferred beater bar is illustrated in FIG. 6. The beater bar may be of any suitable diameter and may contain any number of vibrational elements 10 so long as the vibration imparted to the fabric is sufficient to ensure uniform and complete compaction. The rotational speed of the beater bar will depend on the geometry and number of vibrational elements. A preferred beater bar (see Ex. 1) rotates at 300 to 400 rpm. The beater bar preferably rotates in the direction of fabric movement to assist in forcing the knit elements together.

In processing the knitted fiberglass fabric of the present invention, a length of fabric is heat-set while the fabric is in a compacted form. Preferably, the fabric is compacted and then wound onto a cylindrical core so large batches ("jumbo rolls") can be heat set at one time in a single oven. Care must be taken to avoid applying undue tension to the fabric (particularly after combustion of the elastomeric yarn and before the heat set has occurred) which would distort the knots and loops. In order to accomplish this the fabric is preferably surface wound using a winder which isolates the weight of the fabric from the winding process. A preferred winder uses a center shaft to support the roll. Additional layers of fabric are added to the roll by a surface winding element (i.e., a roller which contacts the outer edge of the fabric roll). The surface winding element rotates thereby rotating the fabric roll. This is in contrast to a winder which merely drives the center shaft of the fabric roll.

In order to further prevent undesirable stretching of the fabric during batch process desizing and heat setting, the jumbo roll can be placed in the oven on its side (i.e., one edge of the cylinder down). This orientation minimizes "tear dropping" of the roll, i.e., sagging of the fabric, which distorts the round roll. Alternatively, the jumbo roll can be otherwise supported to prevent such sagging.

A continuous heat-setting process may also be used in which a length of fabric is first compacted by the vibration process described herein and then the compacted fabric is supported on a moving conveyor system and passed through an oven for a sufficient time and temperature to achieve heat setting of the fabric. Notably, when short lengths of fabric are so processed the ends of the elastomeric yarn should be held in relation to the ends of the fiberglass yarns so as to cause compaction. Otherwise the elastomeric yarns may merely slip against the fabric as they relax and not cause compaction of the knit fabric.

The heat-setting step may be performed in a number of conventional ways known to the art. In heat-setting a small piece of fiberglass fabric, e.g., 25 centimeters of tape, in a single layer, a temperature of 425° C. for three minutes has been found to be sufficient. Equivalent setting at lower temperatures is possible, but longer time is required. In general, batch processes require a longer residence time at the selected temperature due to the mass of glass fabric which must be heated and the need to remove all traces of sizing material which may undesirably color the final fabric.

The optimum heat-setting process described above is sufficient in most cases to remove the sizing from the fabric. However, the process of the present invention may also be practiced using partially heat-desized or a chemically-desized fabric. Chemical desizing processes are described in U.S. Pat. Nos. 3,686,725; 3,787,272; and 3,793,686. Heat desizing processes are described in U.S. Pat. No. 4,609,578.

In general, to completely desize the fiberglass tape and not leave any visible residue it is necessary to heat the tape to a temperature between 370 and 430° C. more preferably between 400° and 430° C. The closer you get to 430° C. the shorter the cycle and more efficient the operation. Although the tape could be cleaned at higher temperatures, this may cause permanent degradation of the fiberglass fabric. For example, when the temperature of the fabric exceeds 480° C. and especially when the temperature exceeds 540° C. the tensile strength of the knit decreases very rapidly. When the tape is exposed to temperatures over 590° C. it becomes very brittle and wrapping a cast using normal tension is precluded. A preferred heat desizing cycle raises the oven temperature to about 430° C. and maintains that temperature until the tape is clean (e.g., about 6–8 hours in a recirculating oven). However, obtaining this result is somewhat complicated since the tape's temperature is affected by both the heat of the oven and the heat of combustion resulting from burning the sizing and/or any organic yarn (i.e., the elastomeric yarn) which may be present.

Controlling the exotherm from organic material in the knit is essential and can be accomplished most easily and economically by limiting the total amount of added organic material (e.g., sizing and elastomeric yarn) which must be removed. In order to knit a fiberglass yarn without excessive damage a sizing is preferably present. Preferably the amount of sizing utilized is the minimum level necessary to prevent damage during knitting. On fiberglass, a preferred amount of sizing is between 0.75 and 1.35% (based on weight of the fabric). In addition to this sizing, in order to compact the tape, an elastomeric yarn is added to the fabric. Since this yarn adds substantially to the total level of organic material in the fabric it is important to limit the amount added. This can be accomplished by several methods.

First, one may limit the number of elastomeric yarns used. Placing the elastomeric yarn in every wale is believed to be unnecessary and undesirable o due to the resulting high exothermic temperature during desizing. Preferably the knit has an elastomeric yarn in-laid across the tape only in wales spaced 2 to 6 needles apart. Most preferably the knit has an elastomeric yarn in-laid across the tape only in wales spaced 3 to 4 needles apart. Normally, the spacing is uniform across the web but since the preferred pattern used crosses only a single needle it can be varied without modification to the knitting machine.

Second, one may decrease the denier of the elastomeric yarn. Preferably, the lowest denier yarn which when stretched has sufficient tensile force to compact the tape should be used. For preferred fiberglass fabrics the preferred elastomeric yarns are about 100 to 500 denier, more preferably about 200 to 300 denier measured in the relaxed condition.

In order to apply a compacting force the elastomeric yarns are knit into the fabric under tension. Typically, the yarns are stretched between 50 and 600% during knitting, more preferably the yarns are stretched between 100 and 500%, and most preferably the yarns are stretched between 200 and 400%.

Finally, it has been observed that the jumbo's winding tension can greatly influence the exothermic temperature rise due to combustion and therefore adversely affect web integrity. In general, jumbos wound under higher tension tend to reach a lower peak temperature and have a greater web integrity than those wound more loosely. It is believed that the organic content of more tightly wound jumbos burn more slowly and therefore have lower peak internal temperatures. While not intending to be bound by theory, this result is believed to be due to oxygen starvation within the jumbo. Within a jumbo (i.e., away from the surface of the roll) the availability of oxygen is controlled by the diffusion rate into the jumbo. Careful control of the roll's permeability to oxygen can be utilized to control the rate of combustion of the organic material.

The fabric is preferably cooled prior to application of the resin. The resin selected to apply to the heat-set fabric is dictated by the end-use of the product. For orthopedic casting materials, suitable resins are well-known and described for example, in U.S. Pat. Nos. 4,376,438; 4,433,680; 4,502,479; and 4,667,661 which are herein incorporated by reference. The presently most preferred resins are the moisture-curable isocyanate-terminated polyurethane prepolymers described in the aforementioned patents. Alternatively, one may employ one of the resin systems described herein. The amount of such resin applied to the fiberglass tape to form an orthopedic casting material is typically an amount sufficient to constitute 35 to 50 percent by weight of the final "coated" tape. The term "coated" or "coating" as used herein with respect to the resin refers generically to all conventional processes for applying resins to fabrics and is not intended to be limiting.

The heat set fabrics of this invention are preferably coated with a curable resin using a low tension coating process. It is particularly critical to avoid applying tension to the fabric after the resin has been applied to the tape and allowed to wet into the fabric as the resin may act as a lubricant thereby facilitating movement of the fabric yarns. Preferably, the tension on the fabric is kept below 0.05 N/mm width after coating and wetting with the resin. More preferably, the tension on the fabric is kept below 0.017 N/mm width after coating and wetting with the resin. Prior to coating with the resin higher tensions may be used since the frictional forces required to move the yarns relative to one another are higher. The preferred coating methods are those which require no tension and/or wound up very rapidly after the resin coating is applied.

To insure storage stability of the coated tape, it must be properly packaged, as is well known in the art. In the case of water-curable isocyanate-terminated polyurethane prepolymer resin systems, moisture must be excluded. This is typically accomplished by sealing the tape in a foil or other moisture-proof pouch.

In one embodiment of the present invention, a fiberglass fabric which further comprises a plurality of elastomeric yarns is knit and compacted according to the process described herein, and then heat set in the compacted form while also removing the elastomeric yarns. The compacted fabric is then coated with a curable resin. There are many advantages to this process over conventional knitting processes. First, unlike traditional uncompacted knit fiberglass fabrics, the fabric produced by this method has increased extensionability. Furthermore, the elastomeric yarn, when in its unstretched state, provides support to the fabric during subsequent collecting operations (such as when winding a large jumbo roll) thereby preventing undesirable extension of the fabric prior to it being heat set. The finished fabric of this embodiment comprises only noncombustible yarns and retains its compacted form as a result of the heat setting of the fiberglass yarns.

Suitable fabrics, after compaction, are compacted to between about 30 and 90 percent of their original dimension. More preferably, the fabric is compacted to between about 50 and 80 percent of its original dimension. Most preferably, the fabric is compacted to between about 60 and 75 percent of its original dimension.

The curable or hardenable resins useful in this invention are resins which can be used to coat a sheet material and which can then be cured or hardened to reinforce the sheet material. For example, the resin is curable to a crosslinked thermoset state. The preferred curable or hardenable resins are fluids, i.e., compositions having viscosities between about 5 Pa s and about 500 Pa s, preferably about 10 Pa s to about 100 Pa s.

The resin used in the casting material of the invention is preferably any curable or hardenable resin which will satisfy the functional requirements of an orthopedic cast. Obviously, the resin must be nontoxic in the sense that it does not give off significant amounts of toxic vapors during curing which may be harmful to either the patient or the person applying the cast and also that it does not cause skin irritation either by chemical irritation or the generation of excessive heat during cure. Furthermore, the resin must be sufficiently reactive with the curing agent to insure rapid hardening of the cast once it is applied but not so reactive that it does not allow-sufficient working time to apply and shape the cast. Initially, the casting material must be pliable and formable and should adhere to itself. Then in a short time following completion of cast application, it should become rigid or, at least, semi-rigid, and strong to support loads and stresses to which the cast is subjected by the activities of the wearer. Thus, the material must undergo a change of state from a fluid-like condition to a solid condition in a matter of minutes.

The preferred resins are those cured with water. Presently preferred are urethane resins cured by the reaction of a polyisocyanate and a polyol such as those disclosed in U.S. Pat. No. 4,131,114. A number of classes of water-curable resins known in the art are suitable, including polyurethanes, cyanoacrylate esters, epoxy resins (when combined with moisture sensitive catalysts), and prepolymers terminated at their ends with trialkoxy- or trihalo-silane groups. For example, U.S. Pat. No. 3,932,526 discloses that 1,1-bis(perfluoromethylsulfonyl)-2-aryl ethylenes cause epoxy resins containing traces of moisture to become polymerized.

Resin systems other that those which are water-curable may be used, although the use of water to activate the hardening of an orthopedic casting tape is most convenient, safe and familiar to orthopedic surgeons and medical casting personnel. Resin systems such as that disclosed in U.S. Pat. No. 3,908,644 in which a bandage is impregnated with difunctional acrylates or methacrylates, such as the bismethacrylate ester derived from the condensation of glycidyl methacrylate and bisphenol A (4,4'-isopropylidenediphenol) are suitable. The resin is hardened upon wetting with solutions of a tertiary amine and an organic peroxide. Also, the water may contain a catalyst. For example, U.S. Pat. No. 3,630,194 proposes an orthopedic tape impregnated with acrylamide monomers whose polymerization is initiated by dipping the bandage in an aqueous solution of oxidizing and reducing agents (known in the art as a redox initiator system). The strength, rigidity and rate of hardening of such a bandage is subjected to the factors disclosed herein. Alternatively, hardenable polymer dispersions such as the aqueous polymer dispersion disclosed in U.S. Pat. No. 5,169,698, which is herein incorporated by reference, may be used in the present invention.

Some presently more preferred resins for use in the present invention are water-curable, isocyanate-functional prepolymers. Suitable systems of this type are disclosed, for example, in U.S. Pat. No. 4,411,262, and in U.S. Pat. No. 4,502,479. Preferred resin systems are disclosed in U.S. Pat. No. 4,667,661 and U.S. patent application Ser. No. 07/376,421 which are herein incorporated by reference. The following disclosure relates primarily to the preferred embodiment of the invention wherein water-curable isocyanate-functional prepolymers are employed as the curable resin. A water-curable isocyanate-functional prepolymer as used herein means a prepolymer derived from polyisocyanate, preferably aromatic, and a reactive hydrogen compound or oligomer. The prepolymer has sufficient isocyanate-functionality to cure (i.e., to set or change from a liquid state to a solid state) upon exposure to water, e.g., moisture vapor, or preferably liquid water.

It is preferred to coat the resin onto the fabric as a polyisocyanate prepolymer formed by the reaction of an isocyanate and a polyol. Suitable isocyanates include 2,4-toluene diisocyanate, 2,6-toluene diisocyanate, mixture of these isomers, 4,4'-diphenylmethane diisocyanate, 2,4'-diphenylmethane diisocyanate, mixture of these isomers together with possible small quantities of 2,2'-diphenylmethane diisocyanate (typical of commercially available diphenylmethane diisocyanate), and aromatic polyisocyanates and their mixtures such as are derived from phosgenation of the condensation product of aniline and formaldehyde. It is preferred to use an isocyanate which has low volatility such as diphenylmethane diisocyanate (MDI) rather than a more volatile material such as toluene diisocyanate (TDI). Typical polyols for use in the prepolymer system include polypropylene ether glycols (available from Arco Chemical Co. under the trade name Arcol™ PPG and from BASF Wyandotte under the trade name Pluracol™), polytetramethylene ether glycols (Polymeg™ from the Quaker Oats Co.), polycaprolactone diols (Niax™ PCP series of polyols from Union Carbide), and polyester polyols (hydroxyl terminated polyesters obtained from esterification of dicarboxylic acids and diols such as the Rucoflex™ polyols available from Ruco division, Hooker Chemical Co.). By using high molecular weight polyols, the rigidity of the cured resin can be reduced.

An example of a resin useful in the casting material of the invention uses an isocyanate known as Isonate™ 2143L available from the Upjohn Company (a mixture containing about 73% of MDI) and a polypropylene oxide polyol from Arco known as Arcol™ PPG725. To prolong the shelf life of the material, it is preferred to include from 0.01 to 1.0 percent by weight of benzoyl chloride or another suitable stabilizer.

The reactivity of the resin once it is exposed to the water curing agent can be controlled by the use of a proper catalyst. The reactivity must not be so great that: (1) a hard film quickly forms on the resin surface preventing further penetration of the water into the bulk of the resin; or (2) the cast becomes rigid before the application and shaping is complete. Good results have been achieved using 4-[2-[1-methyl-2-(4-morpholinyl)ethoxy]ethyl] morpholine (MEMPE) prepared as described in U.S. Pat. No. 4,705,840, the disclosure of which is incorporated by reference, at a concentration of about 0.05 to about 5 percent by weight.

Foaming of the resin should be minimized since it reduces the porosity of the cast and its overall strength. Foaming occurs because carbon dioxide is released when water reacts with isocyanate groups. One way to minimize foaming is to reduce the concentration of isocyanate groups in the prepolymer. However, to have reactivity, workability, and ultimate strength, an adequate concentration of isocyanate groups is necessary. Although foaming is less at low resin contents, adequate resin content is required for desirable cast characteristics such as strength and resistance to peeling. The most satisfactory method of minimizing foaming is to add a foam suppressor such as silicone Antifoam A (Dow Corning), or Antifoam 1400 silicone fluid (Dow Corning) to the resin. It is especially preferred to use a silicone liquid such as Dow Corning Antifoam 1400 at a concentration of about 0.05 to 1.0 percent by weight. Water-curable resins containing a stable dispersion of hydrophobic polymeric particles, such as disclosed in U.S. patent application Ser. No. 07/376,421 and laid open as European Published Patent Application EPO 0 407 056, may also be used to reduce foaming.

Also included as presently more preferred resins in the present invention are non-isocyanate resins such as water reactive liquid organometallic compounds. These resins are especially preferred as an alternative to isocyanate resin systems. Water-curable resin compositions suitable for use in an orthopedic cast consist of a water-reactive liquid organometallic compound and an organic polymer. The organometallic compound is a compound Of the formula $(R^1O)_xMR^2_{(y-x)}$ wherein: each $R^1$ is independently a $C_1-C_{100}$ hydrocarbon group, optionally interrupted in the backbone by 1–50 nonperoxide -O-, -S-, -C(O)-, or groups; each $R^2$ is independently selected from the group consisting of hydrogen and a $C_1-C_{100}$ hydrocarbon group, optionally interrupted in the backbone by 1–50 nonperoxide -O-, -S-, -C(O)-, or groups; x is an integer between 1 and y, inclusive; y is the valence of M; and M is boron, aluminum, silicon, or titanium. The organic polymer is either an addition polymer or a condensation polymer. Addition polymers are preferably utilized as the organic polymer constituent. Particularly useful addition polymers are those made from ethylenically unsaturated monomers. Commercially available monomers, from which such addition polymers can be formed, include but are not limited to, ethylene, isobutylene, 1-hexene, chlorotrifluoroethylene, vinylidene chloride, butadiene, isoprene, styrene, vinyl napthalene, ethyl acrylate, 2-ethylhexyl acrylate, tetrahydrofurfuryl acrylate, benzyl acrylate, poly-(ethylene oxide) monoacrylate, heptafluorobutyl acrylate, acrylic acid, methyl methacrylate, 2-dimethylaminoethyl methacrylate, 3-methacryloxypropyltris-(trimethylsiloxy)silane, isobutyl methacrylate, itaconic acid, vinyl acetate, vinyl stearate, N,N-dimethylacrylamide, tert-butyl acrylamide, acrylonitrile, isobutyl vinyl ether, N-vinyl pyrrolidinone, vinyl azlactone, glycidyl methacrylate, 2-isocyanatoethyl methacrylate, maleic anhydride, vinyl triethoxysilane, vinyl tris(2-methoxyethoxy)silane, and 3-(trimethoxysilyl-)propyl methacrylate. Polymers bearing hydrolyzable functionality are preferred. An acidic or basic catalyst may be used to accelerate the water cure of these compositions. Strong acid catalysts are preferred.

Also included as presently more preferred resins in the instant invention are alkoxysilane terminated resins, i.e., prepolymers or oligomers, having a number average molecular weight of about 400–10,000, preferably about 500–3,000. A polymer forms upon contacting the alkoxysilane terminated prepolymer with water as a result of condensation of molecules of this prepolymer with other molecules of the same prepolymer. Each molecule of the prepolymer or oligomer contains at least one hydrolyzable terminal alkoxysilane group. Compounds of Formula I useful in the resin compositions of the present invention may contain one to six terminal alkoxysilane groups per molecule. Preferably, the alkoxysilane terminated resin is a urethane-based resin, i.e., a prepolymer containing -NH-C(O)-O-group(s), or a urea resin, i.e., a prepolymer containing or a resin containing both urea and urethane groups. More preferably, the resin is urea/urethane-based.

The water-reactive alkoxysilane terminated resin having at least one hydrolyzable terminal alkoxysilane group per molecule is preferably a compound of the formula (Formula I):

wherein:

Q is a polyol residue;

W is -NH-C(O)-X(R²₂₋ₙ₋q)- or -X-C(O)-NH-;

X is

—O—, or —S—;

Y is

-O-,-S-, carbamylthio (-S-C(O)-NH-), carbamate (-O-C(O)-NH-), or substituted or N-substituted ureido (-N(C(O)-NH-)-);

$R^1$ is a substituted or unsubstituted divalent bridging $C_1-C_{200}$ hydrocarbon group, optionally interrupted in the backbone by 1–50 nonperoxide -O-, -C(O)-, -S-, -SO₂-, -NR⁶-, amide (-C(O)-NH-), ureido (-NH-C(O)-NH-), carbamate (-O-C(O)-NH-), carbamylthio (-S-C(O)-NH-), unsubstituted or N-substituted allophonate (-NH-C(O)-N(C(O)-O-)-), unsubstituted or N-substituted biuret (-NH-C(O)-N(C(O)-NH)-), and N-substituted isocyanurate groups;

$R^2$ can be present or absent, and is selected from the group consisting of H and a substituted or unsubstituted $C_1-C_{20}$ hydrocarbon group, optionally interrupted in the backbone by 1–10 nonperoxide-O-, -C(O)-, -S-, -SO₂-, or -NR⁶- groups;

$R^3$ is a substituted or unsubstituted divalent bridging $C_1-C_{20}$ hydrocarbon group, optionally interrupted in the backbone by 1–5 nonperoxide -O-, -C(O)-, -S-, -SO₂-, or -NR⁶- groups;

$R^4$ is a $C_1-C_6$ hydrocarbon group or $-N=C(R^7)_2$;

each $R^5$ and $R^7$ is independently a $C_1-C_6$ hydrocarbon group;

$R^6$ is a H or a $C_1-C_6$ hydrocarbon group;

n=1–2 and q=0–1, with the proviso that when X is N, n+q=1, and when X is S or O, n+q=2;

u = the functionality of the polyol residue = 0–6, with the proviso that when u=0, the compound of Formula I is m=2–3; and z=1–3.

It is to be understood that each "$R^3-Si(R^5)_{3-m}(OR^4)_m$" moiety can be the same or different. When used in Formula I, the Y and $R^1$ groups that are not symmetric, e.g., amide (-C(O)-NH-) and carbamylthio (-S-C(O)-NH-) groups, are not limited to being bound to adjacent groups in the manner in which these groups are represented herein. That is, for example, if $R^1$ is carbamate (represented as -O-C(O)-NH-), it can be bound to Y and W in either of two manners: -Y-O-C(O)-NH-W- and -W-O-C(O)-NH-Y-.

Herein, when it is said that "each" $R^5$ and $R^7$ is "independently" some substituent group, it is meant that generally there is no requirement that all $R^5$ groups be the same, nor is there a requirement that all $R^7$ groups be the same. As used herein, "substituted" means that one or more hydrogen atoms are replaced by a functional group that is nonreactive, e.g., to hydrolysis and/or condensation and noninterfering with the formation of the cured polymer.

In preferred materials $R^1$ is selected from the group consisting of a substituted or unsubstituted $C_1-C_{200}$ alkyl, a substituted or unsubstituted $C_1-C_{200}$ acyl, and groups of up to 50 multiples of a $C_3-C_{18}$ cycloalkyl, a $C_7-C_{20}$ aralkyl, and a $C_6-C_{18}$ aryl. By this, it is meant that $R^1$ can be a long chain containing, for example, up to 50 repeating $C_6-C_{18}$ aryl groups. More preferably, $R^1$ is selected from the group consisting of a substituted or unsubstituted $C_1-C_{100}$ alkyl, a substituted or unsubstituted $C_1-C_{100}$ acyl, and groups of up to 30 multiples of a $C_5-C_8$ cycloalkyl, and a $C_6-C_{10}$ aryl. Most preferably, $R^1$ is selected from the group consisting of a $C_1-C_{20}$ alkyl, a $C_1-C_8$ acyl, and groups of up to 5 multiples of a $C_5-C_8$ cycloalkyl, and a $C_6-C_{10}$ aryl. In each of the preferred $R^1$ groups, the backbone is optionally interrupted by 1–20 nonperoxide -O-, -C(O)-, -S-, -SO₂-, -NR⁶-, amide, ureido, carbamate, carbamylthio, allophonate, biuret, and isocyanurate groups.

In each of the more preferred $R^1$ groups, the backbone is optionally interrupted by 1–10 nonperoxide -O-, -C(O)-, -S-, -SO₂-, -NR⁶-, amide, ureido, carbamate, carbamylthio, allophonate, biuret, and isocyanurate groups. In each of the most preferred $R^1$ groups, the backbone of each of the $R^1$ groups is not interrupted by any of these groups.

In preferred materials, each of $R^2$ and $R^3$ is independently selected from the group consisting of a substituted or unsubstituted $C_1-C_{20}$ alkyl, a substituted or unsubstituted $C_2-C_{18}$ alkenyl, and groups of up to 10 multiples of a $C_3-C_{18}$ cycloalkyl and a $C_6-C_{18}$ aryl. More preferably, each $R^2$ and $R^3$ is independently selected from the group consisting of a substituted or unsubstituted $C_1-C_{10}$ alkyl, a substituted or unsubstituted $C_2-C_{10}$ alkenyl, a $C_5-C_8$ cycloalkyl, and a $C_6-C_{10}$ aryl. Most preferably, each $R^2$ and $R^3$ is independently selected from the group consisting of a $C_1-C_6$ alkyl, a $C_2$ alkenyl, a $C_5-C_8$ cycloalkyl, and a $C_6$ aryl. In each of the preferred $R^2$ and $R^3$ groups, the backbone is optionally interrupted by 1–5 nonperoxide-O-, -C(O)-, -S-, -SO₂-, and -NR⁶- groups. In optimal resins, the backbone of each of the $R^2$ and $R^3$ groups is not interrupted by any of these groups.

In preferred materials, each of $R^4$, $R^5$, $R^6$, and $R^7$ is independently a $C_1-C_6$ alkyl group. More preferably, each is a $C_1-C_3$ alkyl group. A single prepolymer according to Formula I can be used in the resin composition of the present invention. Alternatively, a mixture of several different prepolymers according to Formula I can be used in the resin composition.

Optionally, the scrims of the present invention are coated with a resin which incorporates microfiber fillers. These preferred orthopedic bandages enjoy many benefits, for example, resins which incorporate microfiber fillers exhibit: a dramatic increase in strength when coated on the backings of the present invention; an increased "early strength" upon curing; an improved durability and increased modulus; better layer-to-layer lamination strength; a lower exotherm upon setting; and a lower effective resin cost compared to resins which do not incorporate such microfiber fillers. In addition, resin suspensions employing the microfiber fillers of the present invention exhibit generally very little increase in resin viscosity—thereby ensuring easy unwind of the casting bandage and good handling properties such as drapability. Suitable microfibers for use in the present invention include those microfiber fillers disclosed in U.S. patent application Ser. No. 08/008,755 which is herein incorporated by reference.

In addition to the application of the present invention to the field of orthopedic casting tapes, other uses may include wrapping and/or joining pipes, cables or the like; patching or bridging gaps to provide a surface for filling and repairs; etc.

The following examples are offered to aid in understanding of the present invention and are not to be construed as limiting the scope thereof. Unless otherwise indicated, all parts and percentages are by weight.

EXAMPLES

Ring strength was measured as described in the following procedure. A cylindrical ring comprising 6 layers of the resin-coated material was formed by taking a roll of the resin-coated material from its storage pouch and immersing the roll completely in deionized water having a temperature of about 27° C. for about 30 seconds. The width of the ring formed was the same as the width of the resin-coated material employed, namely, 7.62 cm or 10.2 cm. The roll of resin-coated material was then removed from the water and the material was wrapped around a 5.08 cm diameter mandrel covered with a thin stockinet (such as 3M Synthetic Stockinet MS02) to form 6 complete uniform layers using a controlled wrapping tension of about 45 grams per centimeter width of material. Each cylinder was completely wound within 30 seconds after its removal from the water. After 7 to 20 minutes from the initial immersion in water, the cured cylinder was removed from the mandrel. Ring strength was determined 24 hours after initial immersion in water, i.e., those samples were allowed to cure for 24 hours in a controlled atmosphere of 25° C.±2° C. and 55%±5% relative humidity prior to testing.

At the appropriate time each cylinder was then placed in a fixture in a commercial testing machine, e.g., an Instron 1122 instrument, and compression loads were applied to the cylindrical ring sample along its exterior and parallel to its axis. The cylindrical ring was placed lengthwise between the two bottom bars of the fixture (the bars being 1.9 cm wide, 1.3 cm in height, and 15.2 cm long), with the bars spaced about 4 cm apart. The inside edges of the bars were machined to form a curved surface having a 0.31 cm radius. A third bar (0.63 cm wide, 2.5 cm high, and 15.2 cm long) was then centered over the top of the cylinder, also parallel to its axis. The bottom or contacting edge of the third bar was machined to form a curved surface having a 0.31 cm radius. The third bar was brought down to bear against and crush the cylinder at a speed of about 5 cm/min. The maximum force which was applied while crushing the cylinder was then recorded and divided by the width to yield the "ring strength," which in this particular instance is the "dry strength" (expressed in terms of force per unit length of the cylinder, i.e., newtons/cm). For each material, at least 5 samples were tested, and the average peak force applied was then calculated and reported as the dry "ring strength."

Example 1

Compaction of a Fiberglass Knit Casting Tape

A knit fiberglass fabric (of 76 mm or 102 mm width) containing Cleerspan S-5 490 denier elastomeric yarn was produced with the following parameters: PPG fiberglass ECG 75 1/0 0.7 Z (available from PPG Fiberglass, Pittsburgh, Pa.); Cleerspan S-5 490 denier elastomeric yarn (available from Globe Manufacturing, Fall River, mass.); Mayer Raschel knitter 229 cm 18 gauge (7.1 needles/cm); knit pattern: 2/0, 0/2 (front bar); 0/0, 2/2 (middle bar); and 0/0, 8/8 (back bar); thread up: front and back—full, middle bar: single needle in-lay spaced every third wale; front runner length (fiberglass chain stitch) 419 cm; back runner length (fiberglass lay-in stitch traversing 4 needles) 350 cm; middle bar runner length (elastomeric lay-in stitch traversing one needle) 24.1 cm. Note that the elastomeric yarn was in-laid in phase with the fiberglass inlay and across a single needle in an alternating pattern of: one wale in and the next two wales out. More specifically, the middle bar was threaded so that the elastomeric yarn was placed in every third wale beginning at the second wale from the edge of the fabric. With a runner length of 24.1 cm the elastomeric yarn was elongated approximately 300 to 400 percent during knitting.

A "beater bar", as shown in FIG. 6, comprising a plurality of vibration elements 10 (e.g., six 12.7 mm diameter bars) equally spaced between two hubs 11 (e.g., 200 mm diameter plates comprising a rotation means 12) was rotated around said rotation means at 338 rpm. The aforementioned knit fabric 13 after exiting the knitter 15 was wrapped around the rotating beater bar so as to cover approximately 180 to 220 degrees of the circumference of said bar.

The knit had a surface speed of approximately 0.9 meters per minute as it came off the beater bar. The compacted knit was collected on a center supported surface winder 14 and wound under low tension. Rolls having approximately 166–185 linear meters of fabric had a circumference of approximately 41 cm. Fabric samples prior to heat setting had elongations (percent stretch) when measured under a 22 N load of 56.9% and 52.5% for the 76 mm and 102 mm fabrics respectively (avg. of 10 samples). The percent stretch of the 102 mm fabric is illustrated below in Table 1a.

TABLE 1a

| Load (N/mm width) | Elongation (%) |
|---|---|
| 0.175 | 48.2 |
| 0.219 | 52.5 |
| 0.263 | 55.0* |
| 0.285 | 56.9 |
| 0.438 | 60.1 |

*interpolated data.

Note that at a load of 0.263 N/mm width the fabric had approximately 55% stretch prior to heat setting. The compacted fabric was heat set by hanging the rolls from the center aluminum core and placing the rolls on racks in a recirculated oven. The oven was heated to 315° C. and held for 3 hours before increasing the temperature to 427° C. for 6.5 hours. The heat set/compacted fabric was coated with a moisture curable polyurethane resin having a theoretical NCO/OH ratio of 3.84 and an isocyanate equivalent weight of 357 as described in Table 1b. The heat set fabric was coated using a very low tension coater.

TABLE 1b

| Chemical | Manufacturer | Eqwt. | Wt. % |
|---|---|---|---|
| Isonate 2143L | Dow Chemical | 144.7 | 54.7 |
| pToluenesulfonyl chloride | Akzo | | 0.05 |
| Antifoam DB-100 | Dow Corning | | 0.18 |
| Butylated hydroxytoluene | Shell Chemical | | 0.48 |
| Pluronic F-108 | BASF | | 4.00 |
| MEMPE | 3M | | 1.15 |

TABLE 1b-continued

| Chemical | Manufacturer | Eqwt. | Wt. % |
|---|---|---|---|
| PPG-2025 | Union Carbide[1] | 1016.7 | 25.05 |
| LG-650 | Union Carbide[1] | 86.09 | 5.90 |
| Niax E-562 | Union Carbide[1] | 1719.3 | 8.50 |

[1] Formerly available from Union Carbide now available from Arco Chemical Co., So. Charleston, WV.

The resin was coated on the 7.6 and 10.2 cm wide fabrics produced as described above at a coating weight of 40% by weight. The product was rolled up under low tension on a 1.27 cm diameter polyethylene core into individual rolls having a circumference of approximately 177 mm and were sealed in conventional moisture proof aluminum foil laminate pouches. The product was tested for the properties listed below in Table 1c according to the test methods described above. All values are the mean of 10 samples unless otherwise noted.

TABLE 1c

| Fabric width (mm) | % Stretch (at 22 N load) | Dry strength at 24 hrs. (N/cm with) |
|---|---|---|
| 76 | 52.4 | 101 |
| 102 | 52.0 | 94 |

Notably, very little stretch was lost as a result of the desizing and coating operations.

Various modifications and alterations of this invention will be apparent to those skilled in the art without departing from the scope and spirit of this invention, and it should be understood that this invention is not limited to the illustrative embodiments set forth herein.

What is claimed is:

1. A method of making an orthopedic casting bandage, comprising the steps of:

knitting a fiberglass yarn and a stretched elastomeric yarn to form a fabric;

releasing the tension on the elastomeric yarn as the knit fabric comes off the knitting machine;

vibrating the fabric thereby uniformly compacting said fabric;

heat setting said compacted fabric thereby removing said elastomeric yarn; and coating said fabric with a curable or hardenable liquid resin, wherein said compacted fabric has from about 10% to about 200% extensibility in the elongated direction when a 2.63 N load or force is applied across a 1 cm section of the fabric.

2. A method according to claim 1, wherein said elastomeric yarn is knit into said fabric as a lay-in stitch every 3 to 4 wales.

3. A method according to claim 1, wherein said sheet has from about 25% to about 75% extensibility in the elongated direction when a 2.63 N load or force is applied across a 1 cm section of the fabric.

4. A method according to claim 2, wherein said curable resin is selected from the group consisting of water-curable resins comprising isocyanate-functional prepolymers; water-curable resins comprising a water-reactive liquid organometallic compound and an organic polymer; and alkoxysilane terminated polyurethane prepolymer resins.

5. A method according to claim 1, wherein said resin has a viscosity between about 10 Pa s and 100 Pa s, and wherein said fabric was compacted to between about 20 and 50 percent of its original dimension.

6. A method according to claim 1, wherein said elastomeric yarn is made from fibers selected from the group consisting of synthetic elastomers made from: polybutadiene; polychloroprene; polyisoprene; polyurethane; copolymers of chloroprene and other monomers; copolymers of a diene and styrene; copolymers of a diene and acrylonitrile; copolymers of styrene and acrylonitrile; copolymers and block copolymers of styrene and butadiene; copolymers and block copolymers of styrene and isoprene; terpolymers of styrene, butadiene and isoprene; and ethylene propylene elastomers such as copolymers of ethylene and propylene and terpolymers of ethylene, propylene and a diene; and natural elastomers made from natural rubber.

7. A method according to claim 1, wherein said elastomeric yarn has a denier between 200 and 600.

8. A method according to claim 1, wherein said fabric is vibrated using a beater bar comprising a plurality of bars attached to a hub.

9. A method according to claim 1 further comprising the step of:

collecting said compacted fabric prior to said heat setting step using a center supported surface winder.

10. A method according to claim 1, wherein said coating operation causes less than 0.05 N/mm width tension to be applied to said fabric.

* * * * *